United States Patent

Soto et al.

[11] Patent Number: 5,866,069
[45] Date of Patent: *Feb. 2, 1999

[54] LIQUID REPELLANT SILICONE-TREATED GAS-PERMEABLE MATERIAL FOR STERILIZATION

[75] Inventors: Toby A. Soto, Fort Worth; David Feld; Xiaolan Chen, both of Arlington, all of Tex.

[73] Assignee: Johnson & Johnson Medical Inc., New Brunswick, N.J.

[*] Notice: This patent issued on a continued prosecution application filed under 37 CFR 1.53(d), and is subject to the twenty year patent term provisions of 35 U.S.C. 154(a)(2).

[21] Appl. No.: 613,370

[22] Filed: Mar. 11, 1996

Related U.S. Application Data

[62] Division of Ser. No. 333,848, Nov. 3, 1994, abandoned.

[51] Int. Cl.⁶ .................... A61L 2/14; A61L 2/20
[52] U.S. Cl. .................. 422/28; 8/147; 427/387
[58] Field of Search ..................... 427/535, 344, 427/387; 8/470, 499, 147, 128.3; 523/206; 524/588; 422/20, 22, 28

[56] References Cited

U.S. PATENT DOCUMENTS

| | | | |
|---|---|---|---|
| 3,617,187 | 11/1971 | Chitani et al. | 8/115.5 |
| 4,557,946 | 12/1985 | Sacher et al. | 427/41 |
| 4,803,256 | 2/1989 | Luckenbach | 525/420 |

FOREIGN PATENT DOCUMENTS

| | | |
|---|---|---|
| 0 177 364 A3 | 4/1986 | European Pat. Off. . |
| 177364 | 9/1986 | European Pat. Off. . |
| 0 207 417 A1 | 1/1987 | European Pat. Off. . |
| 207417 | 7/1987 | European Pat. Off. . |
| 507760A1 | 7/1992 | European Pat. Off. . |
| 0507 760 A1 | 10/1992 | European Pat. Off. . |
| 2007449 | 12/1970 | Germany . |
| WO 81/02809 | 10/1981 | WIPO . |

OTHER PUBLICATIONS

"The Surface Phenomena of Silicone Rubber Under the Influence of Impinging Plasmas" Liang, et al., From Tsinghua University, Peoples Republic of China, pp. 142–145, no date.

"Plasma Surface Treatment of Nylon Fabrics by Flurocarbon Compounds" Iriyama, et al., *Journal of Applied Polymer Science,* vol. 39, pp. 249–264 (1990).

"Water–repellent textile fabric production by applying . . . " Derwent Publication Ltd. Abstract of Japanese Application No. 87–180452, May 1987.

*Primary Examiner*—Robert E. Sellers
*Attorney, Agent, or Firm*—Knobbe, Martens, Olson & Bear, LLP

[57] ABSTRACT

Material that is to be used in wrapping medical items or in making gowns, drapes, and the like is treated with silicone to make it liquid repellent. The material, after being sterilized by an oxidizing plasma process, still retains its repellency.

5 Claims, 2 Drawing Sheets

HYDROPHOBICITY AND COMPOSITION OF TREATED AND UNTREATED POLYETHYLENE BEFORE AND AFTER OXIDIZING PLAZMA STERILIZATION

| SAMPLE | HYDROPHOBICITY | | COMPOSITION | | | | | |
|---|---|---|---|---|---|---|---|---|
| | BEFORE PLASMA | AFTER PLASMA | BEFORE PLASMA | | | AFTER PLASMA | | |
| | | | % F | % O | % C | % F | % O | % C |
| UNTREATED POLYETHYLENE | 5 | 0 | 0.0 | 0.4 | 99.6 | 0.0 | 24.0 | 76.0 |
| DUPONT ZONYL 8070 TREATED POLYETHYLENE | | | | | | | | |
| % SOLID 2.0 | 5 | 0 | 31.6 | 10.5 | 57.6 | 10.4 | 29.5 | 58.8 |
| % SOLID 4.0 | 5 | 4 | 43.3 | 6.5 | 50.2 | 23.4 | 19.9 | 56.9 |
| 3M FC 808 TREATED POLYETHYENE | | | | | | | | |
| % SOLID 4.0 | 5 | 0 | 40.7 | 14.5 | 44.8 | 12.9 | 22.7 | 64.4 |
| | | | % Si | % O | % C | % Si | % O | % C |
| GE SM 2112 SILICONE TREATED POLYETHYLENE | | | | | | | | |
| % SOLID 0.5 | 5 | 5 | 15.7 | 19.2 | 65.2 | 16.9 | 46.2 | 36.9 |
| % SOLID 2.0 | 5 | 5 | 16.3 | 19.2 | 64.5 | 18.8 | 44.8 | 36.4 |

*FIG.1*

HYDROPHOBICITY AND COMPOSITION OF TREATED AND UNTREATED POLYPROPYLENE
BEFORE AND AFTER OXIDIZING PLAZMA STERILIZATION

| SAMPLE | HYDROPHOBICITY | | COMPOSITION | | | | | |
|---|---|---|---|---|---|---|---|---|
| | BEFORE PLASMA | AFTER PLASMA | BEFORE PLASMA | | | AFTER PLASMA | | |
| | | | %F | %O | %C | %F | %O | %C |
| UNTREATED POLYPROPYLENE | 5 | 0 | 0.0 | 0.0 | 100 | 0.0 | 22.9 | 77.1 |
| DUPONT ZONYL 8070 TREATED POLYPROPYLENE | | | | | | | | |
| % SOLID 4.0 | 5 | 0 | 43.1 | 4.8 | 52.1 | 14.8 | 25.3 | 59.9 |
| 3M FC 808 TREATED POLYPROPYLENE | | | | | | | | |
| % SOLID 4.0 | 5 | 0 | 41.4 | 13.6 | 45.0 | 5.2 | 26.4 | 68.3 |
| | | | %Si | %O | %C | %Si | %O | %C |
| GE SM 2112 SILICONE TREATED POLYPROPYLENE | | | | | | | | |
| % SOLID 0.5 | 5 | 5 | 11.1 | 15.5 | 73.4 | 15.2 | 30.9 | 52.9 |
| % SOLID 2.0 | 5 | 5 | 15.9 | 19.8 | 64.2 | 13.7 | 34.2 | 50.0 |

FIG. 2

LIQUID REPELLANT SILICONE-TREATED GAS-PERMEABLE MATERIAL FOR STERILIZATION

This application is a divisional of U.S. patent application Ser. No. 08/333,848, filed Nov. 3, 1994, abandoned.

FIELD OF THE INVENTION

This invention relates to liquid repellent materials that remain repellent after being sterilized, and to treatments that render materials liquid repellent.

BACKGROUND OF THE INVENTION

Many medical applications require materials that are both hydrophobic and that provide a sterile barrier. One such application involves the use of such materials for packaging medical products. However, additional examples of the diverse applications to which such materials can be put include medical gowns, drapes, face masks and the like. It is also desirable in certain instances to form an antimicrobial barrier in container filters, such as Sterion® containers available from Johnson & Johnson Medical, Inc. These container filters are devices for filtering air going into a rigid or flexible container.

Materials which are hydrophobic and that provide a sterile barrier resist penetration by water and water-based liquids, including blood and urine, thereby protecting objects within or on one side of the material from contamination. Such materials are used in drapes and gowns, and as packaging material for medical instruments and supplies, among other uses.

Materials used for these applications are either inherently resistant to contaminating liquids or are chemically treated to impart resistance to contaminating liquids. One commonly used treatment to impart resistance is to apply a fluorocarbon agent to the surface of the material. One such agent is FC-808, a fluoroaliphatic ester produced by Minnesota Mining and Manufacturing Company of St. Paul, Minn. According to the U.S. Pat. No. 2,803,615, incorporated herein by reference, the perfluoro carbon group in the 3M agent is attached to a polymer backbone by a sulfamide group and an ester linkage.

Another currently used agent is ZONYL 8070 agent, a perfluoroalkyl acrylic copolymer available from E.I. DuPont de Nemours & Company, Wilmington, Del. According to U.S. Pat. No. 3,282,905, incorporated herein by reference, the perfluoro carbon group in the DuPont agent is attached to a polymer backbone by an ester linkage.

Both FC-808 agent and ZONYL 8070 agent are used to treat breathable polyolefin-based materials, such as those used in central supply room wraps and gowns. However, when these prior art fluorocarbon agents are applied to materials in a conventional fashion, such as by continuous line application, and the fluorocarbon-treated materials exposed to an oxidizing plasma sterilization process, the treated materials can lose some or all of their liquid repellency.

Thus, there is a need for a practical treatment which will render materials resistant to liquid penetration and cause them to remain repellent after sterilization by an oxidizing plasma process. Ideally, the treatment should be simple to perform. Further, the treatment should be inexpensive enough to permit disposal of the treated material after a single use.

SUMMARY OF THE INVENTION

In one aspect, the present invention provides treating a gas-permeable material with a substance including silicone in an amount sufficient to render the material liquid repellent and able to withstand exposure to an oxidizing plasma sterilizing process without losing its repellency. The invention also includes the material treated in that manner. Preferably, the amount of silicone remaining on the material after treatment is in the range from about 0.4% to about 5.0% silicone by weight, more preferably from about 0.4% to 3.0% by weight.

The invention is further directed to the method of exposing the treated material to an oxidizing plasma and directed to the material that has been so exposed. The silicone-containing substance may be applied by spraying, but preferably is applied by subjecting the material to an aqueous emulsion including a silicone. Preferably, the concentration of silicone in the emulsion is between 0.25 and 35 percent by weight, more preferably between about 0.50 and 4.0 percent by weight. An organic solvent based system can also be employed. Preferred silicones are polydimethylsiloxane, polydiphenylsiloxane, or polymethylphenylsiloxane.

Preferably, the material is a gas permeable, nonwoven material. Some suitable materials are polyolefin, such as polyethylene, and polypropylene.

BRIEF DESCRIPTION OF THE FIGURES

FIG. 1 compares the hydrophobicity and composition of untreated polyethylene, fluorocarbon-treated polyethylene, and silicone-treated polyethylene, both before and after oxidizing plasma sterilization.

FIG. 2 compares the hydrophobicity and composition of untreated polypropylene, fluorocarbon-treated polypropylene and silicone-treated polypropylene, both before and after oxidizing plasma sterilization.

DETAILED DESCRIPTION OF THE PREFERRED EMBODIMENTS

As noted above, it has been discovered that materials, such as fabrics, treated with silicone to impart liquid repellency retain their repellency after being subjected to an oxidizing plasma process. There are a variety of materials suitable for the silicone treatment. These materials can comprise either natural substances or synthetic substances, or can comprise a combination of both natural and synthetic substances, and can be either woven or nonwoven. However, gas-permeable, nonwoven synthetic fabrics are preferable.

Examples of suitable synthetic substances include polyolefin-based materials, such as polyethylene, sold under the trademark TYVEK, available from E.I. DuPont de Nemours & Company, Wilmington, Del., or polypropylene, sold under the trademark KIMGUARD, available from Kimberly-Clark Corporation, Dallas, Tex.

A variety of silicone compounds can be used to treat material in accordance with the present invention. In a preferred embodiment, the silicone substance used to treat the material comprises a siloxane compound. These compounds include one or more monomeric units of siloxane, which is represented by the formula:

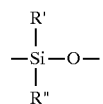

where R' and R" are the same or different organic group or hydrogen. Preferred siloxane compounds are polydimethylsiloxanes, in which both R and R" are methyl.

Other available siloxanes include phenylsiloxane, diphenylsiloxane and methylphenylsiloxane.

The siloxane can also contain functional groups capable of crosslinking with other siloxane molecules. For example, as discussed in more detail below, vinyl groups can be linked to hydrosilane groups (Si—H). Other suitable crosslinking functional groups are well known by those having ordinary skill in the art.

Silicone compounds can be cross-linked by either a "condensation cure" or by "addition cure" of linear prepolymer components. As will be appreciated by those having ordinary skill in the art, condensation cure of silicone is usually initiated by moisture and is often catalyzed by an organo-tin compound. In condensation cure, the prepolymer typically terminates on either end with an —O—R group, such as hydroxy, methoxy, ethoxy or acetate. The addition of water to these compounds in the presence of catalyst results in the linkage of these molecules with loss of ROH. Thus, for the given examples of —O—R, water, methanol, ethanol or acetic acid, respectively, are by-products of the reaction.

As will also be appreciated by those having ordinary skill in the art, addition-cured silicone usually involves the linkage of two silicone components and is catalyzed by a platinum compound, such as chloroplatinic acid. In an exemplary addition-cured system, one of the siloxane components is a divinyl terminated polysiloxane, and the other component is a polyhydrosiloxane in which several of the R' or R" groups are hydrogen. The hydrosilanes serve as cross-linking sites for the vinyl groups on the other component. The amount of hydrosilane can be varied in order to vary the amount of cross-linking, and is preferably between about 15% to about 75% of the siloxane monomers.

A variety of commercially available silicone products are available that have been obtained by either addition cure or by condensation cure. However, for medical applications, addition-cured silicone is generally preferred, in order to avoid the release of the by-products of the condensation cure discussed above, such as methanol, ethanol or acetic acid. For medical grades of addition-cured silicone, the prepolymer components are typically evacuated under very high vacuum to remove volatile organics and low molecular weight oligomers, so that there will be less volatiles and leachables after the silicones are vulcanized.

Commercially available polydimethylsiloxanes that can be used to treat material according to one aspect of the present invention include formulations from General Electric Company (GE), Waterford, N.Y., designated SM 2112, SM 2059, and SM 2138. Other suitable formulations are discussed below and still others will be understood by those with skill in the art with reference to the disclosure herein.

Application of the silicone can be accomplished by spraying one or both of the opposing sides of a sheet of material utilizing known spraying systems. Silicone can also be applied to the material by exposing the material to an aqueous silicone emulsion comprising silicone or an organic solvent-based system including silicone.

Exposure to an aqueous emulsion or an organic solvent-based system can be accomplished by a simple dip-and-squeeze process in which (1) the material to be treated is immersed in the aqueous emulsion or the organic solvent-based system; (2) the material being treated is then passed between two rolls that force the silicone treatment into the material and remove any excess silicone treatment; and (3) the treated material is then heated, preferably in a forced air oven, to remove water or organic solvent from the material and to accelerate the cure of the silicone finish, if curing is required. These processes can be accomplished using a Werner Mathis, A.G. padder and a Werner Mathis, A.G. forced air oven (address: CH 8155 Neiderhasli, Zurich, Switzerland), or can be conducted in a continuous line process using equipment manufactured by Fleissuer Incorporated, 1230 Moores Chapel Road, Charlotte, N.C.

Application of an aqueous emulsion or an organic solvent-based silicone to one side of a material can also be accomplished by the use of a gravure coating process. In this process, the aqueous emulsion or organic solvent-based silicone is first transferred from a bulk silicone emulsion/solvent-based system to an engraved roll by a transfer roll running in the emulsion/solution. The excess emulsion/solution is then removed from the engraved roll by a blade or roll and the remainder of the silicone emulsion/solution is transferred to one side of the material to be treated when it passes between the engraved roll and a basking roll. Either one side or both sides of the material can be treated in this manner.

In one preferred embodiment, the concentration of the silicone in the aqueous emulsion is between about 0.25 and 35.0 percent by weight, more preferably between about 0.50 and 5.0 percent by weight. In a particularly preferred embodiment, the concentration of the silicone in the aqueous emulsion is 0.50 percent by weight. The amount of silicone present on the material after treatment with the aqueous emulsion is in the range of 0.4 percent to 5.0 percent by weight.

After exposing at least one side of the material to the substance comprising silicone, the coated material can be dried to better fix the substance onto the material. Drying can be accomplished, for example, by placing the silicone-treated material in a forced air Werner Mathis, A.G. oven, available from a company by that name located in Zurich, Switzerland, or by other methods that will be understood by those with skill in the art.

After the exposing and drying steps, the treated material is ready to be sterilized by an oxidizing plasma process. In a preferred embodiment, the treated material is first used to wrap or enclose medical supplies or instruments. The package can then be sterilized utilizing an oxidizing plasma process as described hereinbelow, yielding sterilized supplies or instruments that are packaged in liquid repellent, sterile material. The packaged supplies or instruments can be used immediately or stored under appropriate conditions for later use. The treated material can also be sterilized separately by the plasma process.

The assignee of the present invention has developed one particular oxidizing plasma process referred to by the trademark STERRAD. This preferred oxidizing plasma process comprises placing the material in a chamber and applying a vacuum to the chamber. When the pressure is reduced to about 300 milliTorr, hydrogen peroxide is released into the chamber, which increases the pressure. After the gas has penetrated the gas-permeable material and has otherwise been distributed throughout the material being sterilized, the pressure is reduced to about 500 milliTorr, and RF energy is applied to create an oxidizing gas plasma, which sterilizes the items in the chamber. Additional details of the plasma sterilizing process are set forth in U.S. Pat. No. 4,643,876, issued Feb. 17, 1987, to Jacobs et al, the disclosure of which is hereby incorporated by reference.

Effectiveness of the Treatment

The hydrophobicity of materials treated according to the present invention were compared against the hydrophobicity of the same materials uncoated and coated with a conventional fluorocarbon-containing substance, both before and after sterilization by an oxidizing plasma process. Two groups of materials were compared. The first group, as shown in FIG. 1, comprised untreated polyethylene (TYVEK), polyethylene treated with DuPont ZONYL 8070 agent, polyethylene treated with 3M FC-808 agent, and polyethylene (TYVEK) treated with GE SM 2112 Silicone. The second group, as shown in FIG. 2, comprised untreated polypropylene, polypropylene treated with Dupont ZONYL 8070 agent, polypropylene treated with 3M FC-808 agent, and polypropylene treated with GE SM 2112 Silicone.

Both the silicone-containing substances and the fluorocarbon-containing substances were applied to the materials by a standard dip-and-squeeze process, described herein, and were dried in a forced air Werner Mathis, A. G. oven.

After drying, the samples were exposed to a hydrogen peroxide plasma sterilization process utilized in the STERRAD sterilization system, described herein, and then evaluated for hydrophobicity as follows. Water drops were placed on the surface of the material with a medicine dropper held approximately one-quarter inch to one-half inch from the surface. After the drops were allowed to rest on the surface for approximately 15 minutes, both the surface of the material with the drop and the opposing surface were evaluated visually. Each material was given a rating of zero to 5, according to the following scale:

| Rating | Description |
| --- | --- |
| 0 | Complete saturation of the material and spreading of drop away from the original site |
| 1 | Near saturation of material under the drop of fluid, with minor spreading away from the drop |
| 2 | Considerable darkening of the surface (wetting of the surface on more than half of the area of the drop or strike-through to the opposite surface of the material) |
| 3 | Moderate darkening of the surface (wetting of the surface on half or less of the area of the drop or several scattered spots) |
| 4 | Slight darkening of the surface (wetting of the surface on one-quarter to one-third of area of the drop or a few small spots) |
| 5 | No darkening of the surface under the drop |

Electron spectroscopy for chemical analysis (ESCA) was also conducted on the materials, both before and after exposure to the oxidizing plasma, to evaluate the effects of the oxidizing plasma process on the chemical composition of the material surface.

Test Results

Referring now to FIG. 1, there is shown the results of tests comparing the hydrophobicity of polyethylene, both before and after sterilization by an oxidizing plasma, in the untreated state and treated with either a substance comprising silicone according to one aspect of the present invention, or one of two conventional fluorocarbon coatings. As can be seen, untreated polyethylene was highly hydrophobic before exposure to oxidizing plasma, but completely lost its hydrophobicity after exposure to the oxidizing plasma.

Polyethylene treated with ZONYL 8070 agent at a concentration of 2.0 percent solid by weight in the emulsion also lost its hydrophobicity after exposure to oxidizing plasma. When a concentration of 4.0 percent solid by weight in the emulsion of ZONYL 8070 agent was applied to the polyethylene, hydrophobicity was partly retained after exposure to oxidizing plasma.

Polyethylene that had been treated with FC-808 agent was no more hydrophobic after exposure to oxidizing plasma than was untreated polyethylene exposed to oxidizing plasma.

Referring still to FIG. 1, it can be seen that treatment of polyethylene with GE SM 2112 silicone agent at a concentration of 0.5 percent solid in the emulsion resulted in a material that was completely hydrophobic, on the scale set forth above, after exposure to oxidizing plasma. The results were the same when a concentration of 2.0 percent solid of GE SM 2112 silicone in the emulsion was used.

Referring now to FIG. 2, there is shown the results of tests comparing the hydrophobicity of polypropylene, both before and after treatment by oxidizing plasma, in the untreated state and treated with either a substance comprising silicone according to one aspect of the present invention, or one of two conventional fluorocarbon-containing substances. As can be seen, untreated polypropylene was highly hydrophobic before exposure to oxidizing plasma, but completely lost its hydrophobicity after exposure to the oxidizing plasma. Treatment of polypropylene with ZONYL 8070 agent at a concentration of 4.0 percent solid did not increase the hydrophobicity after exposure to oxidizing plasma. Treatment with FC-808 agent having a concentration of 4.0 percent of the solid in the emulsion also did not increase the hydrophobicity after exposure to oxidizing plasma.

By contrast, however, it can be seen that treatment of polypropylene with GE SM 2112 silicone at either a concentration of 0.5 percent solid in the emulsion or 2.0 percent solid in the emulsion, resulted in a material that was completely hydrophobic, on the scale set forth above, after exposure to oxidizing plasma.

The Electron Spectroscopy for Chemical Analysis (ESCA) revealed that plasma oxidation had significantly less effect on the percent of silicone present on the surface of the material than on the percent of fluorine present on the surface of the material. These results are consistent with the observed loss of hydrophobicity. The 3M FC-808 agent appeared to be more sensitive to the oxidizing plasma process than the DuPont Zonyl 8070 agent.

Thus, as shown by these results, treatment with a substance comprising silicone renders the materials hydrophobic before and after sterilization by an oxidizing process, while untreated materials and fluorocarbon treated materials lose either some or all of their hydrophobicity after exposure to the oxidizing plasma. While DuPont Zonyl 8070 treated polyethylene exhibited some hydrophobicity after plasma treatment when treated at 4.0%, this fluorocarbon treatment exhibited zero hydrophobicity when treated at lower concentrations or when used on polypropylene. In contrast, silicone treatment retains substantially all of its hydrophobicity at concentrations at least as low as 0.5% and on a variety of different materials. Thus, considering the availability and cost of the substances comprising silicone, silicone treatment is especially economical, particularly when compared to substances comprising fluorocarbon. Also, the method disclosed herein can be performed using techniques and equipment readily available and adaptable to the present invention.

The present invention can be embodied in other specific forms without departing from its spirit or essential characteristics. The described embodiments are to be considered in all respects only as illustrative and not restrictive. The scope of the invention was, therefore, indicated by the appended claims rather than the foregoing description. All changes which come within the meaning and range of equivalency of the claims are to be embraced within their scope.

We claim:

1. A method for sterilizing an item comprising the steps of:

providing a gas-permeable, liquid repellent material, said material being treated with a substance comprising a liquid repellent silicone thereon such that the material remains gas permeable and liquid repellent;

enclosing the item within the material; and exposing the enclosed item to hydrogen peroxide gas and an oxidizing plasma to effect sterilization of the item, such that the material remains liquid repellent and gas permeable following said exposure.

2. The method of claim 1, wherein the providing step comprises providing a material made of a polyolefin.

3. The method of claim 2, wherein said polyolefin is a polyethylene or a polypropylene.

4. The method of claim 1, wherein the providing step comprises providing a material having a substance comprising a polydimethylsiloxane thereon.

5. The method of claim 1, wherein the providing step comprises providing a substance including at least one of a polydiphenylsiloxane, a polymethylphenylsiloxane, or a combination of any of the foregoing.

* * * * *